United States Patent [19]

Fujii et al.

[11] Patent Number: 5,027,378
[45] Date of Patent: Jun. 25, 1991

[54] INDUSTRIAL COMPUTED TOMOGRAPHY APPARATUS

[75] Inventors: Masashi Fujii; Kiichiro Uyama; Takao Shoji, all of Tokyo; Kenji Arai, Saitama, all of Japan

[73] Assignee: Kabushiki Kaisha Toshiba, Kawasaki, Japan

[21] Appl. No.: 564,613

[22] Filed: Aug. 9, 1990

[51] Int. Cl.⁵ .............................................. G01B 15/06
[52] U.S. Cl. ........................................ 378/11; 378/14; 378/61; 378/10; 378/58
[58] Field of Search ....................... 378/11, 14, 61, 58, 378/10, 4

[56] References Cited

U.S. PATENT DOCUMENTS

4,785,354 11/1988 Nakamura et al. ...................... 378/4

Primary Examiner—Edward P. Westin
Assistant Examiner—Don Wong
Attorney, Agent, or Firm—Foley & Lardner

[57] ABSTRACT

An industrial CT apparatus capable of obtaining a good image quality by a simple configuration. The apparatus is the second generating type incorporating the rotational motions as well as the traverse motions, in which the detector is positioned nearby a center of rotation of the object to be examined. When the object to be examined is a ring shaped object, the detector is positioned inside the center bore of the object. Also, the X-ray is emitted in a form of fan shaped beam whose symmetrical axis is deviated from an axial direction perpendicular to the traverse direction.

8 Claims, 7 Drawing Sheets

INDUSTRIAL COMPUTED TOMOGRAPHY APPARATUS

BACKGROUND OF THE INVENTION

1. Field of the Invention

The present invention relates to a computed tomography (abbreviated hereafter as CT) apparatus for obtaining a tomographic image of an object to be examined by measuring an amount of radiation penetrated through the object to be examined, and in particular, such as CT apparatus adapted to an examination of industrial products.

2. Description of the Background Art

In recent years, various types of a CT apparatus for obtaining a tomographic image of an object to be examined by measuring an amount of radiation penetrated through the object to be examined have been developed for industrial use.

Figure 1:
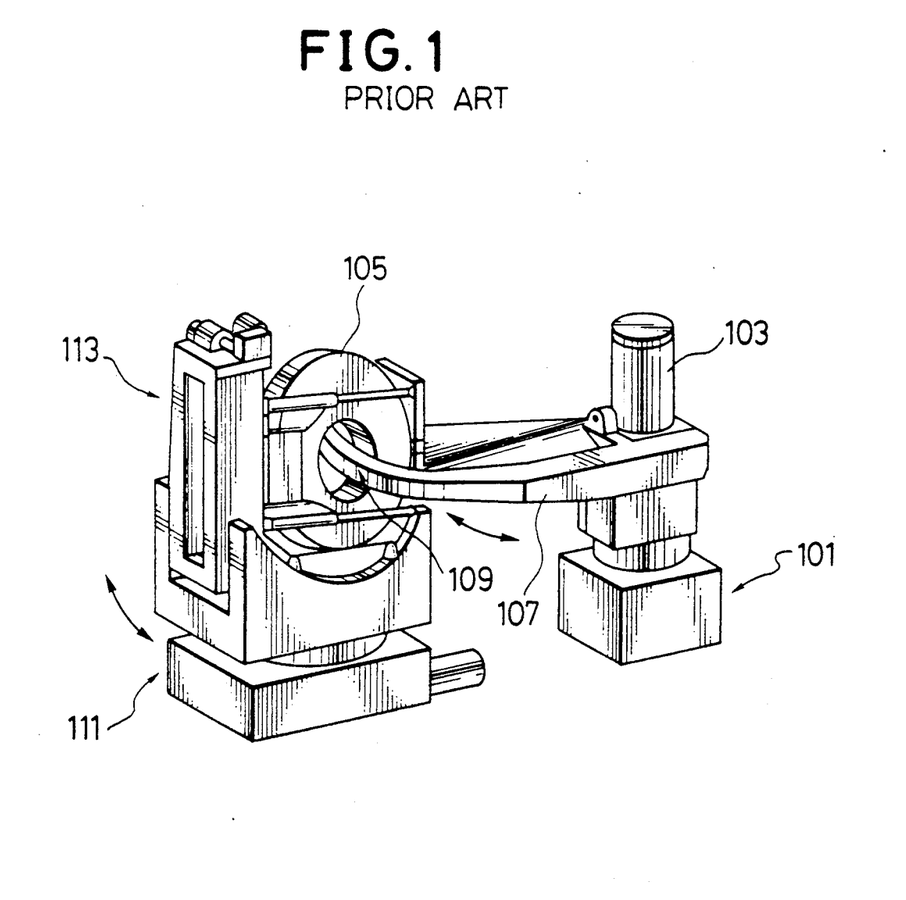
FIG. 1 is a perspective view of an example of a conventional industrial CT apparatus, which belongs to the third generation.

An example of such a conventional industrial CT apparatus is shown in FIG. 1.

This CT apparatus of FIG. 1 is a so called third generation CT apparatus in which the tomographic image is obtained by relative rotational motions of the apparatus and the object to be examined alone, without relative transverse motions.

This CT apparatus comprises a sector scanning unit 101 including an X-ray tube 103 for emitting a fan beam shaped X-ray onto a tire 105 to be examined, and an arm 107 thrusted inside a central bore of the tire 105 which has a plurality of detectors 109 arranged in arc for detecting the X-ray penetrated through one cross section of the tire 105; and a rotation mechanism 111 for holding the tire 105 rotatably around an axis normal to the cross section at a center of the cross section, which also includes a loading mechanism 113 for applying a load pressure on the tire 105 so that the measurement can be performed for the tire 105 in loaded state.

This CT apparatus of FIG. 1 is effective in carrying out the measurement on a ring shaped product, but is also known to have the following problems.

Namely, in a case a high energy X-ray tube is adopted for the X-ray tube 103 in order to increase the energy of the X-ray to be emitted, it is also necessary to use high energy type detectors for the detectors 109.

However, in a third generation CT apparatus, due to the fact that each of the detectors 109 covers a ring shaped data region, i.e., a concentrical area around a scanning center, there is a great possibility of ring shaped artefacts to appear on a displayed image.

Now, in order to prevent the artefacts from appearing, the detectors 109 must satisfy a very stringent requirement regarding a uniformity of their characteristics, and this requires image reconstruction and various corrections such as a sensitivity correction among detection channels (also called an air correction), an offset correction, and a correction of radiation strength fluctuation (also called a reference correction) to be performed extremely carefully, which in turn makes it very difficult and tedious to obtain a good image quality.

Figure 2:
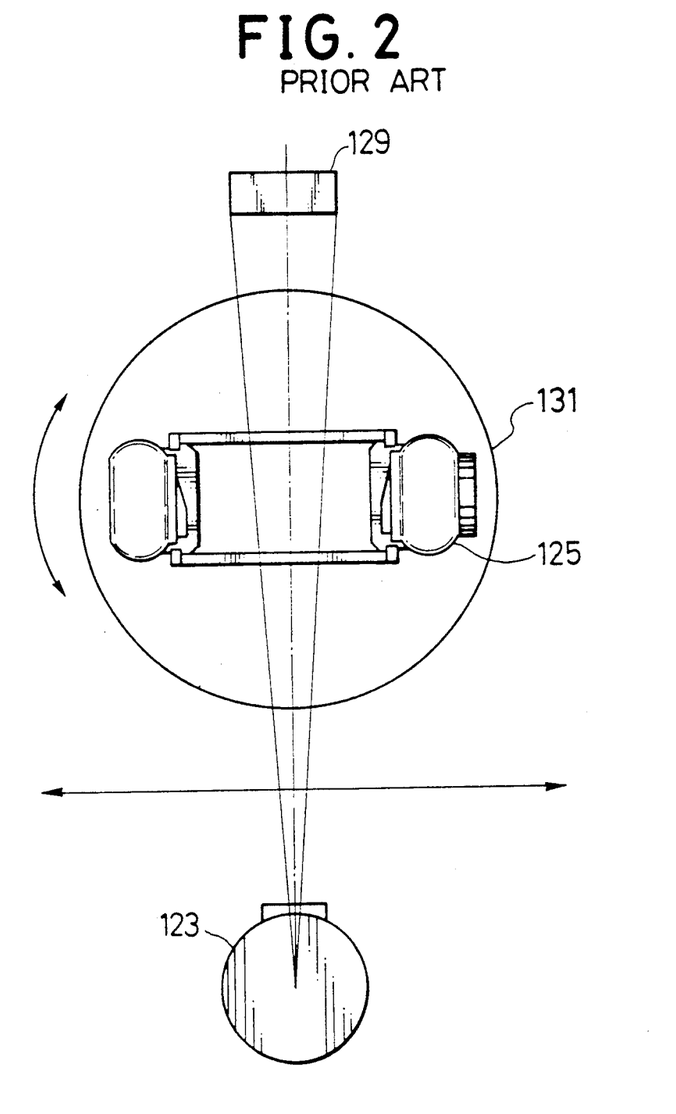
FIG. 2 is a schematic top plan view of another example of a conventional industrial CT apparatus, which belongs to the second generation.

Another example of a conventional industrial CT apparatus is shown in FIG. 2.

This CT apparatus of FIG. 2 is a so called second generation CT apparatus in which the tomographic image is obtained by a combination of relative rotational motions and relative traverse motions of the apparatus and the object to be examined.

Namely, in this apparatus, an X-ray tube 123 for emitting a fan beam shaped X-ray onto a tire 125 to be examined and a detector 129 facing the X-ray tube 123 for detecting the X-ray penetrated through one cross section of the tire 125 are fixedly provided, while the tire 125 is held by a carrier device 131 located between the X-ray tube 123 and the detector 129. The tire 125 is held to be rotatable around an axis normal to the cross section at a center of the cross section and is oscillated back and force in a traverse direction perpendicular to a straight line joining the X-ray tube 123 and the detector 129 while an orientation of the tire 125 is altered for each traverse motion.

SUMMARY OF THE INVENTION

It is therefore an object of the present invention to provide an industrial CT apparatus capable of obtaining a good image quality by a simple configuration.

According to one aspect of the present invention there is provided an industrial computed tomography apparatus, comprising: X-ray tube means for emitting X-ray onto an object to be examined; detector means for detecting the X-ray penetrated through the object to obtain detection data, the detector means being located nearby a center of rotation of the object; means for rotating the object by an increment of a prescribed angle around a normal direction passing through a scanning center on a tomographic imaging plane; means for moving the X-ray tube means and the detector means with respect to the object, in a traverse direction perpendicular to the normal direction; and means for obtaining tomographic image of the object from the detection data obtained by the detector means.

According to another aspect of the present invention there is provided an industrial computed tomography apparatus, comprising: means for rotating the object by an increment of a prescribed angle around a normal direction passing through a scanning center on a tomographic imaging plane; X-ray tube means for emitting X-ray onto an object to be examined, the X-ray tube means emitting the X-ray in a form of a fan shaped beam whose symmetrical axis is deviated from an axial direction perpendicular to the normal direction; detector means for detecting the X-ray penetrated through the object to obtain detection data; means for moving the X-ray tube means and the detector means with respect to the object, in a traverse direction perpendicular to both the axial direction and the normal direction; and means for obtaining tomographic image of the object from the detection data obtained by the detector means.

Other features and advantages of the present invention will become apparent from the following description taken in conjunction with the accompanying drawings.

DETAILED DESCRIPTION OF THE PREFERRED EMBODIMENTS

Figure 3:
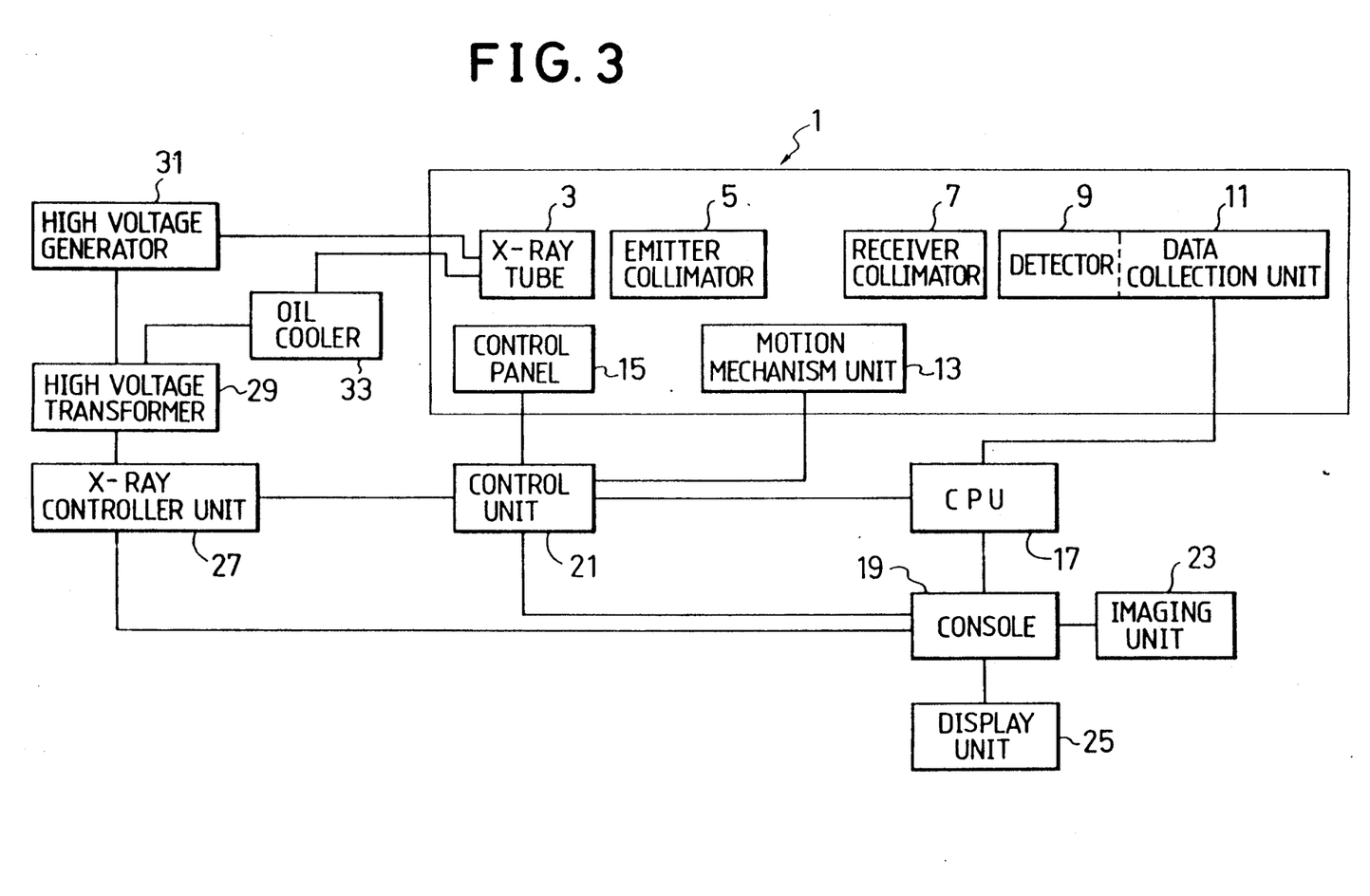
FIG. 3 is a schematic block diagram for one embodiment of an industrial CT apparatus according to the present invention.

Referring now to FIG. 3, there is shown one embodiment of an industrial CT apparatus according to the present invention.

In this embodiment, the CT apparatus has a detection device 1 comprising an X-ray tube 3 for continuously emitting an X-ray onto an object to be examined; an emitter collimator 5 for shaping the X-ray emitted by the X-ray tube 3 in a stable fan shaped beam; a detector 9 for detecting the X-ray penetrated through the object to be examined; a receiver collimator 7 for limiting directions from which the X-ray is received by the detector 9; a data collection unit 11 for processing detection data outputted from the detector 9 into projection data by applying A/D conversion and other pre-processings; a motion mechanism unit 13 including a traversing mechanism unit, a shifting mechanism unit, a rotating mechanism unit, and a positioning mechanism unit, all of which will be described in detail below; and a control panel 15 for entering commands to specify various imaging conditions.

The detector 9 possesses 44 channels, each of which is made of a detector block constructed by a photo diode and scintillator.

The CT apparatus of this embodiment also has a CPU 17 for controlling operations of an entire CT apparatus, as well as for carrying out a reconstruction of a tomographic image of the object to be examined from the projection data obtained by the data collection unit 11. In this reconstruction, various corrections such as an off-set correction, a reference correction, and an air correction are applied to the projected data.

The CT apparatus of this embodiment further includes a console 19 for facilitating various control operations by a user, a display unit 25 for displaying the imaging conditions entered at the control panel 15 along with the tomographic image reconstructed by the CPU 17, an imaging unit 23 for taking a picture of the image displayed on the display unit 25, an X-ray controller unit 27 for controlling the emission of the X-ray from the X-ray tube 3, a high voltage generator 31 and a high voltage transformer 29 for supplying a high voltage power for activating the X-ray tube 3, an oil cooler 33 for cooling the X-ray tube 3 and the high voltage transformer 29, and a control unit 21 for controlling the X-ray controller 27 and the motion mechanism unit 13 under the control from the control panel 15, CPU 17, or console 19.

Figure 4:
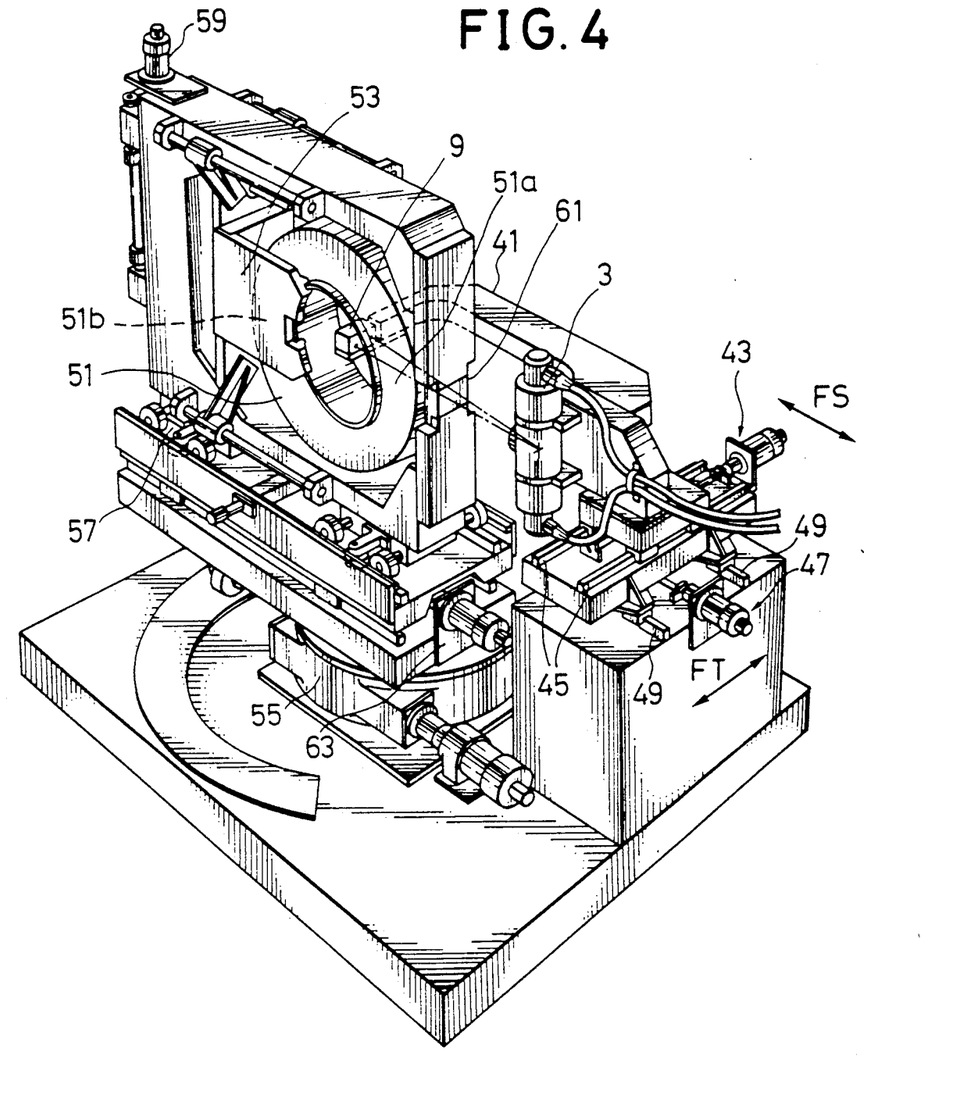
FIG. 4 is a perspective view of the industrial CT apparatus of FIG. 3.

Referring now to FIG. 4, a detail construction of the detection device 1 will be described.

The X-ray tube 3 and the detector 9 of the detection device 1 is attached to an arm 41, so that their relative position is fixed and they can be moved in a traverse direction, together by means of the traversing mechanism unit as described below. On the arm 41, the detector 9 is fixed to a position facing the X-ray tube 3, and this detector 9 is thrusted into a central bore of a ring shaped object to be examined, which in this example is a tire 51.

Figure 5:
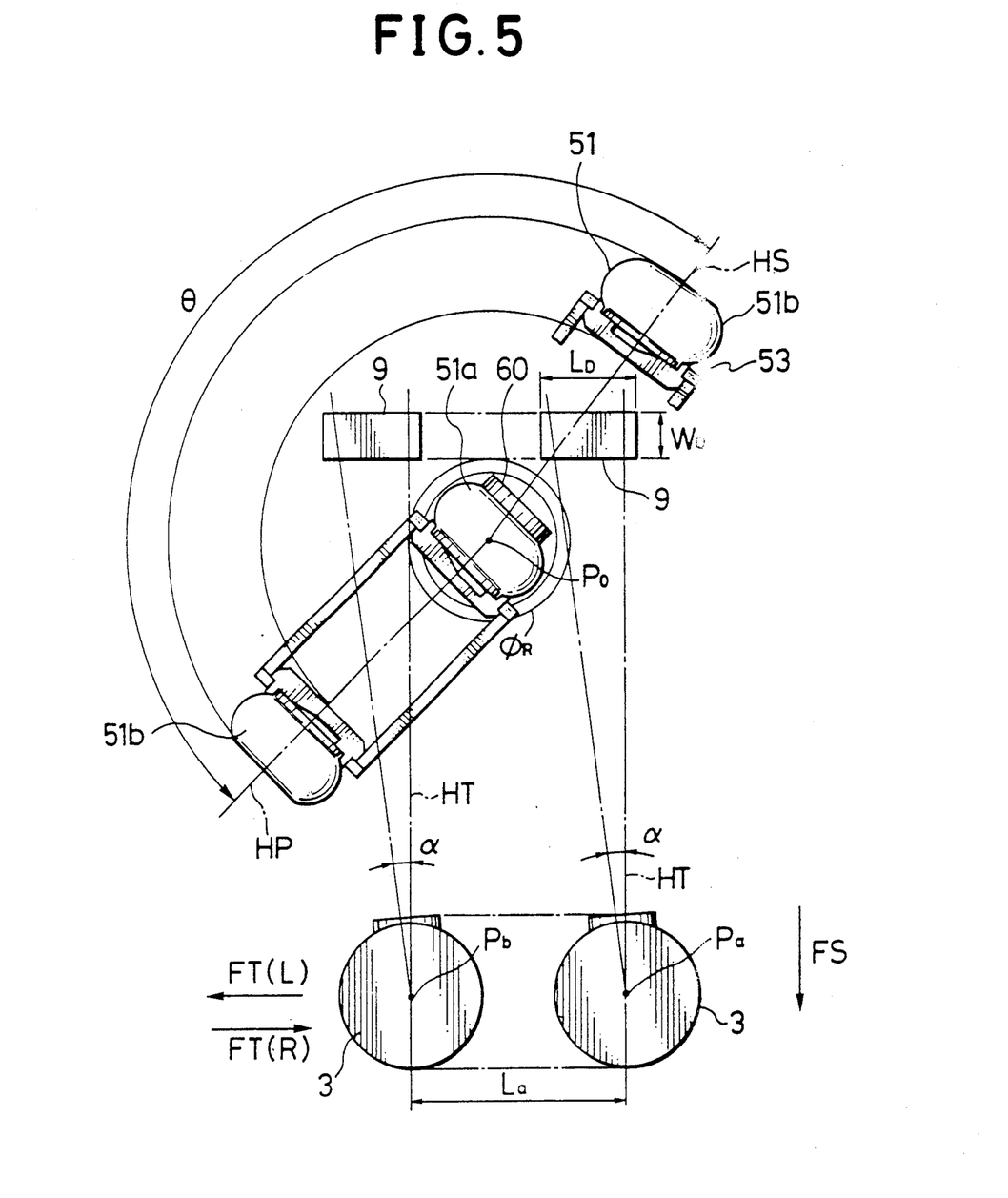
FIG. 5 is a schematic top plan view of the industrial CT apparatus of FIG. 3 for explaining its operation in one exemplary situation.

More specifically, as shown in FIG. 5, the X-ray emitted from the X-ray tube 3 is shaped into a fan shaped beam limited in a fan angle $\alpha$ on a plane by means of the first collimator 5, where the fan angle $\alpha$ is taken asymmetrically, from an axial line HT, which is perpendicular to a traverse direction FT of a traverse motion of the arm 41, to the left when looked from the X-ray tube 3 side toward a position of the detector 9. Accordingly, the detector 9 of a length $L_D$ and a width $W_D$ is located at a position deviated from a point on the axial line HT to the left, in order to receive the deviated X-ray beam.

The traverse mechanism unit 43 of the motion mechanism 13 is located at a root of the arm 41 behind the X-ray tube 3, and has a pair of rails 45 in the traverse direction FT such that the arm 41 can be moved along these rails 45, in order to provide the traverse motion of the X-ray tube 3 and the detector 9.

The shifting mechanism unit 47 of the motion mechanism unit 13 is located underneath the traverse mechanism unit 43, and has a pair of rails 49 in the axial direction FS perpendicular to the traverse direction FT such that the traverse mechanism unit 43 can be moved along these rails 49 in the axial direction FS.

The rotating mechanism unit 55 of the motion mechanism unit 13 is located below a space between the X-ray tube 3 and the detector 9, and is for holding the tire 51, by means of a clamper 53, as well as rotating the tire 51 around a normal line at a scanning center on a tomographic imaging plane.

On this rotating mechanism unit 55, the clamper 53 for holding the tire 51 is provided on a movable carrier 57 for sliding the tire 51 into an appropriate position with respect to the rotating mechanism unit 55 at a time of mounting the tire 51. This movable carrier 57 is also equipped with a loading mechanism unit 59 and a receiving plate 61 for applying a loading pressure on the tire 51 mounted on the movable carrier 57, so that the measurement can be carried out for the tire 51 under the loading pressure.

The positioning mechanism unit 63 is located between the rotating mechanism unit 55 and the movable carrier 57, and is for adjusting the position of the tire 51 with respect to the rotating mechanism unit 55 such that the normal line at a scanning center on a tomographic imaging plane in the tire 51 can be aligned with a rotation axis of the rotating mechanism unit 55.

Referring now to FIG. 5, the operation of this industrial CT apparatus for an exemplary case of using the tire 51 of an ordinary size will be described, which is performed according to a flow chart of FIG. 6.

First, at the step S1, the X-ray tube 3 and the tire 51 are positioned to a scanning start positions. More specifically, a center of X-ray emission in the X-ray tube 3 is placed at a position Pa, while a tomographic imaging plane 51a in the tire 51 is aligned with a plane of the X-ray beam from the X-ray tube 3. The tire 51 is held to be rotatable around the scanning center Po, for an angle $\theta$ ($\theta = 180 - \alpha$) between a line HS to a line HP. At the beginning of the scanning, a cross section 51b at a symmetrical position with respect to the tomographic imaging plane 51a is located on the line HS.

Next, at the step S3, the X-ray tube 3 and the detector 9 are moved in the traverse direction FT(L) toward the left for a distance La by the traverse mechanism unit 43, while the X-ray tube 3 is emitting the fan shaped X-ray beam of fan angle α. As a result, a scanning region $\phi_R$ is scanned, and the 44 channel detection data Da is obtained by the detector 9.

Next, at the step S5, whether a predetermined number of traverse motions have been performed or not is determined. This predetermined number is obtained by dividing 180° by the fan angle α. If the predetermined number of traverse motions have been performed, the process terminates at the step S9, whereas otherwise the step S7 is taken next.

At th step S7, the tomographic imaging plane 51a is rotated in a counter-clockwise direction around the scanning center Po for an angle α equal to the fan angle of the X-ray, by the rotating mechanism unit 55.

Then, the process returns to the step S3, at which the X-ray tube 3 and the detector 9 are moved in the traverse direction FT(R), opposite to that of the previous traverse motion, toward the right for a length La by the traverse mechanism unit 43, while the X-ray tube 3 is emitting the fan shaped X-ray beam of fan angle α. As a result, the scanning region $\phi_R$ is scanned again, and another 44 channel detection data Db is obtained by the detector 9.

Figure 7:
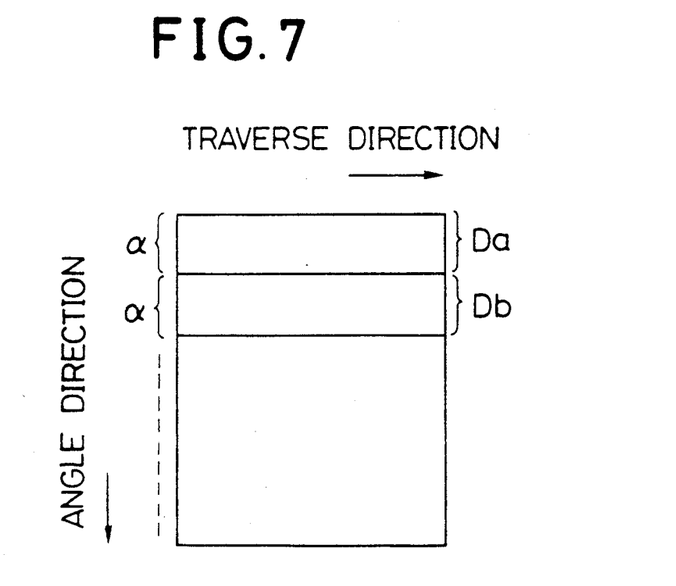
FIG. 7 is an illustration of a data field to be obtained by the industrial CT apparatus of FIG. 3.

The similar procedure is repeated for the predetermined number of times, by which the detection data Da, Db, etc. are obtained as shown in FIG. 7, from which the tomographic image can be constructed.

At the end of the scanning, the center of X-ray emission in the X-ray tube 3 may be located at a position Pb, while the cross section 51b at a symmmetrical position with respect to the tomographic imaging plane 51a is located on the line HP, at which this side of the tire 51 comes closest to the X-ray tube 3. Here, in this embodiment, a symmetrical axis of the X-ray beam is deviated to the left by an angle α/2, so as to provide a sufficient clearance between the X-ray beam and this side of the tire 51 such that this side of the tire 51 does not interfere with the X-ray beam even at this closest position.

Figure 8:
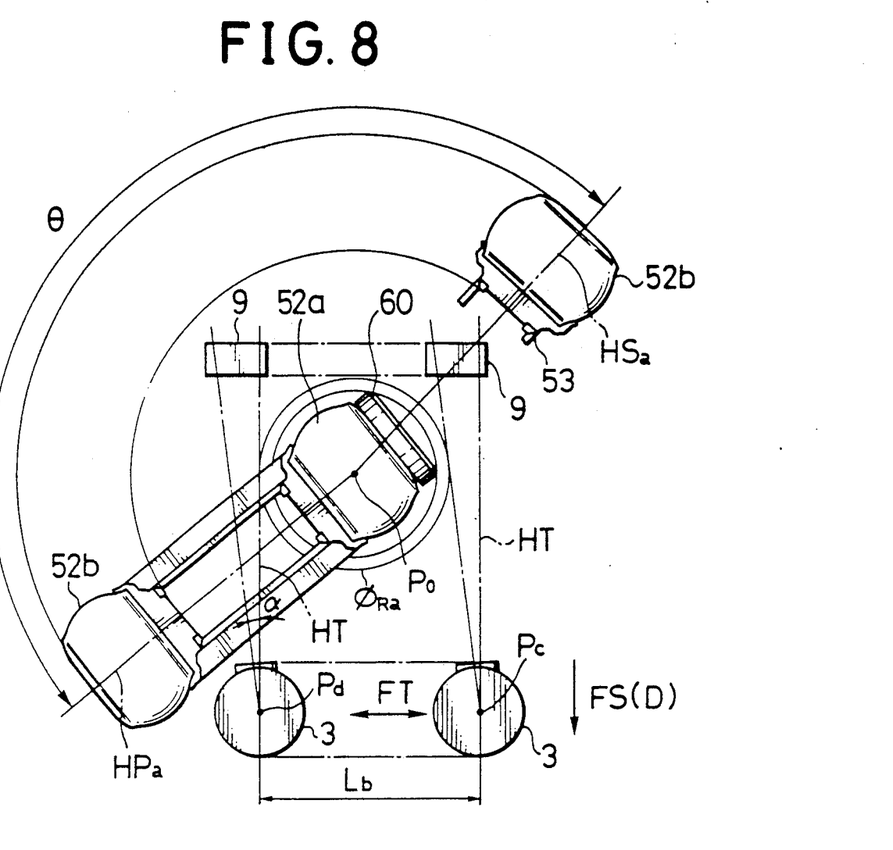
FIG. 8 is a schematic top plan view of the industrial CT apparatus of FIG. 3 for explaining its operation in another exemplary situation.

Referring now to FIG. 8, the operation of this industrial CT apparatus for another exemplary case of using the tire 51 of a larger size than that in the previous example will be described.

Here, a tire 52 has a size larger than the tire 51 of the previous example, and therefore the scanning region $\phi_{R\,a}$ is also larger than the scanning region $\phi_R$ of the previous example. Accordingly, the X-ray tube 3 and the detector 9 have to be traversed for a distance Lb longer than the distance La of the previous example.

In addition, in order to avoid the interference of the tire 52 and the X-ray beam, the X-ray tube 3 and the detector 9 are moved downward in the axial direction FS(D) perpendicular to the traverse direction FT, by the shifting mechanism unit 47, so that the X-ray tube 3 is located at a position Pc at the beginning of the scanning, and at a position Pd at the end of the scanning.

Figure 6:
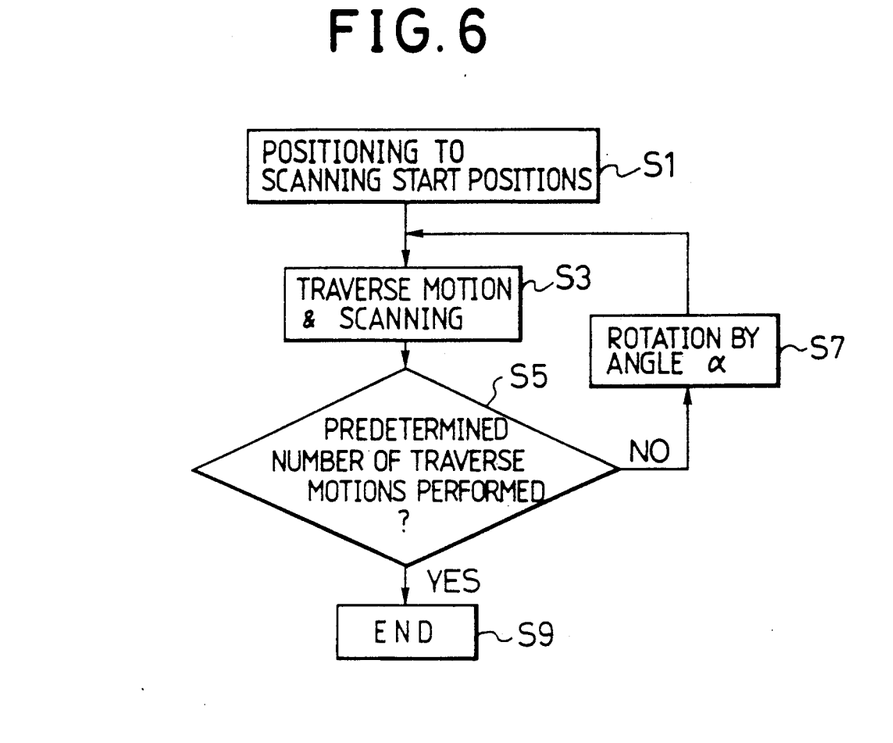
FIG. 6 is a schematic flow chart for the operation of the industrial CT apparatus of FIG. 3.

With such a positioning, the scanning is carried out as in the previous example, according to the flow chart of FIG. 6.

As in the previous example, at the end of the scanning, the center of X-ray emmision in the X-ray tube 3 may be located at a position Pd, while a cross section 52b at a symmetrical position with respect to the tomographic imaging plane 52a is located on the line HPa, at which this side of the tire 52 comes closest to the X-ray tube 3. Again, in this embodiment, a symmetrical axis of the X-ray beam is deviated to the left by an angle α/2, so as to provide a sufficient clearance between the X-ray beam and this side of the tire 52 such that this side of the tire 52 does not interfere with the X-ray beam even at this closest position.

As described, according to this embodiment, it is possible to provide an industrial CT apparatus capable of obtaining a better image quality than a conventional industrial CT apparatus of the second generation, because the detector 9 is positioned closer to the X-ray tube 3 so that the S/N ratio can be improved, and the scanning can be performed more efficiently.

Moreover, according to this embodiment, it is possible to provide an industrial CT apparatus capable of obtaining a good image quality by a configuration simpler than that of a conventional industrial CT apparatus of the third generation, because the artefacts can be eliminated without demanding extremely careful corrections.

Figure 9:
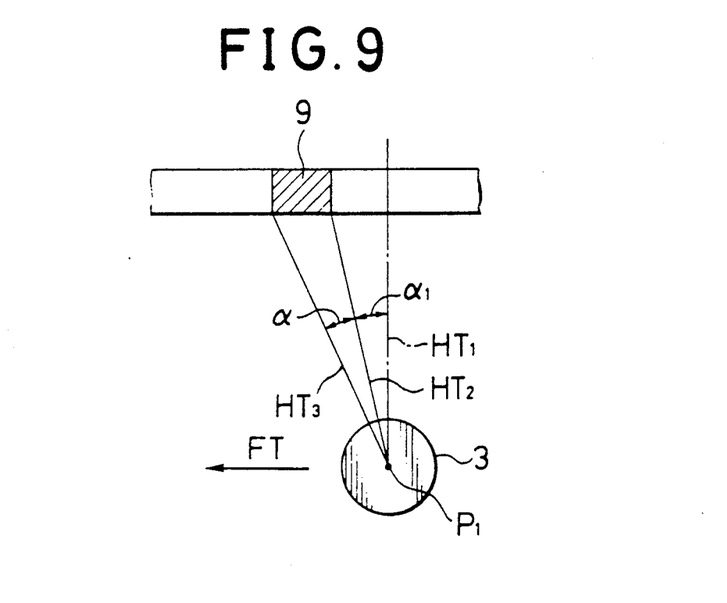
FIG. 9 is a schematic illustration of a part of the industrial CT apparatus of FIG. 3 for explaining one possible modification.

Referring now to FIG. 9, there is shown one modification on the embodiment described above according to the present invention.

In this modification, the symmetrical axis of the X-ray beam is deviated more than that in the above embodiment. Namely, the X-ray beam is limited in the fan angle α, which is now taken from a line $HT_2$ deviated from an axial line $HT_1$ perpendicular to the traverse direction FT by an angle α1, to a line $HT_3$ deviated from the axial line $HT_1$ by an angle α+α1.

With this configuration, the clearance between the X-ray beam and one side of the tire can be enhanced further than in the above embodiment.

Besides this, many modifications and variations of the above embodiments may be made without departing from the novel and advantageous features of the present invention. Accordingly, all such modifications and variations are intended to be included within the scope of the appended claims.

What is claimed is:

1. An industrial computed tomography apparatus, comprising:
   X-ray tube means for emitting X-ray onto an object to be examined;
   detector means for detecting the X-ray penetrated through the object to obtain detection data, the detector means being located within a central bore of the object;
   means for rotating the object by an increment of a prescribed angle around a normal direction passing through a scanning center on a tomographic imaging plane;
   means for moving the X-ray tube means and the detector means with respect to the object, in a traverse direction perpendicular to the normal direction; and
   means for obtaining tomographic image of the object from the detection data obtained by the detector means.

2. The apparatus of claim 1, wherein the object to be examined has a ring shape.

3. The apparatus of claim 1, further comprising means for shifting the X-ray tube means and the detector means in an axial direction perpendicular to both the normal direction and the traverse direction.

4. The apparatus of claim 1, wherein the X-ray tube means emit the X-ray in a form of a fan shaped beam whose symmetrical axis is deviated from an axial direction perpendicular to both the normal direction and the traverse direction.

5. An industrial computed tomography apparatus, comprising:

- means for rotating the object by an increment of a prescribed angle around a normal direction passing through a scanning center on a tomographic imaging plane;
- X-ray tube means for emitting X-ray onto an object to be examined, the X-ray tube means emitting the X-ray in a form of a fan shaped beam whose symmetrical axis is deviated from an axial direction perpendicular to the normal direction;
- detector means for detecting the X-ray penetrated through the object to obtain detection data;
- means for moving the X-ray tube means and the detector means with respect to the object, in a traverse direction perpendicular to both the axial direction and the normal direction; and
- means for obtaining tomographic image of the object from the detection data obtained by the detector means.

6. The apparatus of claim 5, wherein the detector means is located within a central bore of the object.

7. The apparatus of claim 6, wherein the object to be examined has a ring shape.

8. The apparatus of claim 5, further comprising means for shifting the X-ray tube means and the detector means in an axial direction perpendicular to both the normal direction and the traverse direction.

* * * * *